United States Patent [19]

Behan

[11] Patent Number: 4,641,647

[45] Date of Patent: Feb. 10, 1987

[54] DEVICE FOR SECURING RESPIRATORY APPLIANCE DURING RESPIRATORY THERAPY

[75] Inventor: Diane E. Behan, Greenbelt, Md.

[73] Assignee: Sheryl L. Taylor, Seabrook, Md.; a part interest

[21] Appl. No.: 699,927

[22] Filed: Feb. 8, 1985

[51] Int. Cl.$^4$ ............................................. A61M 15/08
[52] U.S. Cl. ........................... 128/207.18; 128/207.11; 128/DIG. 26; 2/173; 2/197; 2/201
[58] Field of Search ........... 128/136, 151, 163, 201.22, 128/201.23, 201.24, 201.25, 201.26, 203.29, 204.11, 205.25, 206.12, 206.27, 207.11, 207.13, 207.17, 207.18, DIG. 26; 604/179; 2/422, 209.1, 185 R, 188, 189, 197, 199, 417, 171, 173, 183, 200-201

[56] References Cited

U.S. PATENT DOCUMENTS

| 804,272 | 12/1905 | Schwarz | 128/207.18 |
|---|---|---|---|
| 807,597 | 12/1905 | Carpenter | 128/201.23 |
| 1,177,383 | 3/1916 | Claren | 128/206.29 |
| 2,259,817 | 10/1941 | Hawkins | 128/207.18 |
| 2,353,643 | 7/1944 | Bulbulian | 128/207.11 |
| 2,414,405 | 1/1947 | Bierman et al. | 128/201.23 |
| 3,013,556 | 12/1961 | Galleher, Jr. | 128/207.11 |
| 4,367,735 | 1/1983 | Dali | 128/207.18 |
| 4,406,283 | 9/1983 | Bir | 128/207.18 |
| 4,485,495 | 12/1984 | Lunt | 2/197 |

FOREIGN PATENT DOCUMENTS

| 277770 | 9/1914 | Fed. Rep. of Germany | 128/206.15 |
|---|---|---|---|
| 15148 | 8/1956 | Fed. Rep. of Germany | 128/206.12 |
| 780746 | 2/1935 | France | 128/207.11 |
| 50041 | 3/1941 | Netherlands | 128/207.11 |
| 82/0003548 | 10/1982 | PCT Int'l Appl. | 128/207.13 |
| 100907 | 2/1941 | Sweden | 128/207.11 |
| 27599 | of 1903 | United Kingdom | 128/207.13 |
| 23021 | of 1913 | United Kingdom | 128/205.25 |
| 188612 | 11/1922 | United Kingdom | 128/205.12 |
| 203741 | 9/1923 | United Kingdom | 128/207.11 |

OTHER PUBLICATIONS

"Trimed", Trimed Incorporated, A Subsidiary of Integrated Circuits, Inc., pp. 1-4 (advertising brochure).
Avery, M. E. and Fletcher, B. D., The Lung and Its Disorders in the Newborn, W. B. Saunders Co., Philadelphia, PA, 1974, pp. 70 & 72.

Primary Examiner—Henry J. Recla
Assistant Examiner—Karin M. Reichle
Attorney, Agent, or Firm—Fleit, Jacobson, Cohn & Price

[57] ABSTRACT

A device for securing a respiratory appliance during respiratory therapy having a head covering made of a material which conforms to the shape of the patient's head, and two elongated thread-like members positioned on opposite sides of the head covering at points which approximately correspond to the temporal areas of the patient's head, the thread-like members being adjustable to vary the distance between the respiratory appliance and the head covering so that the respiratory appliance is securely positioned within the patient's nares.

6 Claims, 3 Drawing Figures

DEVICE FOR SECURING RESPIRATORY APPLIANCE DURING RESPIRATORY THERAPY

BACKGROUND OF THE INVENTION

1. Field of the Invention

The present invention relates to a device which is used to secure respiratory appliance to a patient during respiratory therapy. The present invention is particularly suitable for attaching nasal prongs to a newborn infant when administering continuous positive airway pressure (CPAP).

Continuous positive airway pressure refers to ventilation assisted by a flow of air delivered at a constant pressure throughout the respiratory cycle. It is performed for patients who can initiate their own respirations but who are not able to maintain adequate arterial oxygen levels without assistance. CPAP may be given through a ventilator and endotracheal tube, through nasal prongs, or through a nasopharyngeal tube.

Newborn infants who are delivered prior to term are subject to various disorders which can complicate their neonatal course. Many premature infants develop respiratory distress syndrome (RDS) or hyaline membrane disease (HMD) requiring oxygen therapy. It has been found that continuous positive airway pressure has a significant therapeutic effect on infants with hyaline membrane disease. Indeed, the major use of CPAP has been to improve arterial $P_{O2}$, in order to reduce $F_{1O2}$, in infants with HMD who do not require assisted ventilation. Avery, *Neonatology* (2d Ed.) 1981. However, continuous positive airway pressure is useful in treating many other respiratory problems in both infants and adults.

The basic components of a system for applying CPAP include (1) a source of gas; (2) a device for varying the pressure in the system; (3) a manometer; and (4) a means for connecting the system to the patient's airway. Since most premature infants are quite small, the most common means for applying CPAP is through nasal prongs. Due to the sensitivity of newborn infants to trauma of even the slightest degree, it is important that the respiratory appliance remain securely in place and functioning at all times. However, many of the devices available today are difficult to secure to an infant's airway due to the infant's small size, the need to move the infant regularly, and the infant's own natural movements.

2. Description of the Prior Art

Prior to the present invention, many methods were tried in an effort to secure nasal prongs to an infant's airway. One of the most common means of attaching nasal prongs to the infant is by securing the prongs with conventional surgical masks having the planar portion of the mask applied to the back of the head and secured to the extensions on either side of the prongs with the strings which extend from the mask. Also, string or gauze is often tied around the circumference of the infant's head. However, a premature infant's skull is quite soft immediately after birth and a face mask or string tends to leave ridges in the infant's skull or change the shape of the head entirely. Prior art methods of securing the nasal prongs also can cause pressure sores, or excoriation, and the prior art means are easily dislodged when the infant is moved or moves naturally.

Thus, it is an object of the present invention to provide a device for securing a respiratory appliance or the like on a patient during respiratory therapy in such a way as to distribute evenly over the head the tugging pressure caused by movement of the appliance.

It is a further object of the present invention to provide a device for securing a respiratory appliance or the like during respiratory therapy which can be adjusted to fit securely on the individual patient in need of therapy.

A still further object of the present invention is to provide a device for securing a respiratory appliance or the like during respiratory therapy which allows complete freedom of head movement without dislodging or dislocating the respiratory appliance.

SUMMARY OF THE INVENTION

These and other objects are accomplished according to the present invention by providing a head covering made of a material which conforms to the shape of a head and to which is attached an adjustable connecting means for securing the respiratory appliance in the proper position for delivering respiratory therapy.

DESCRIPTION OF THE PREFERRED EMBODIMENT

Figure 1:
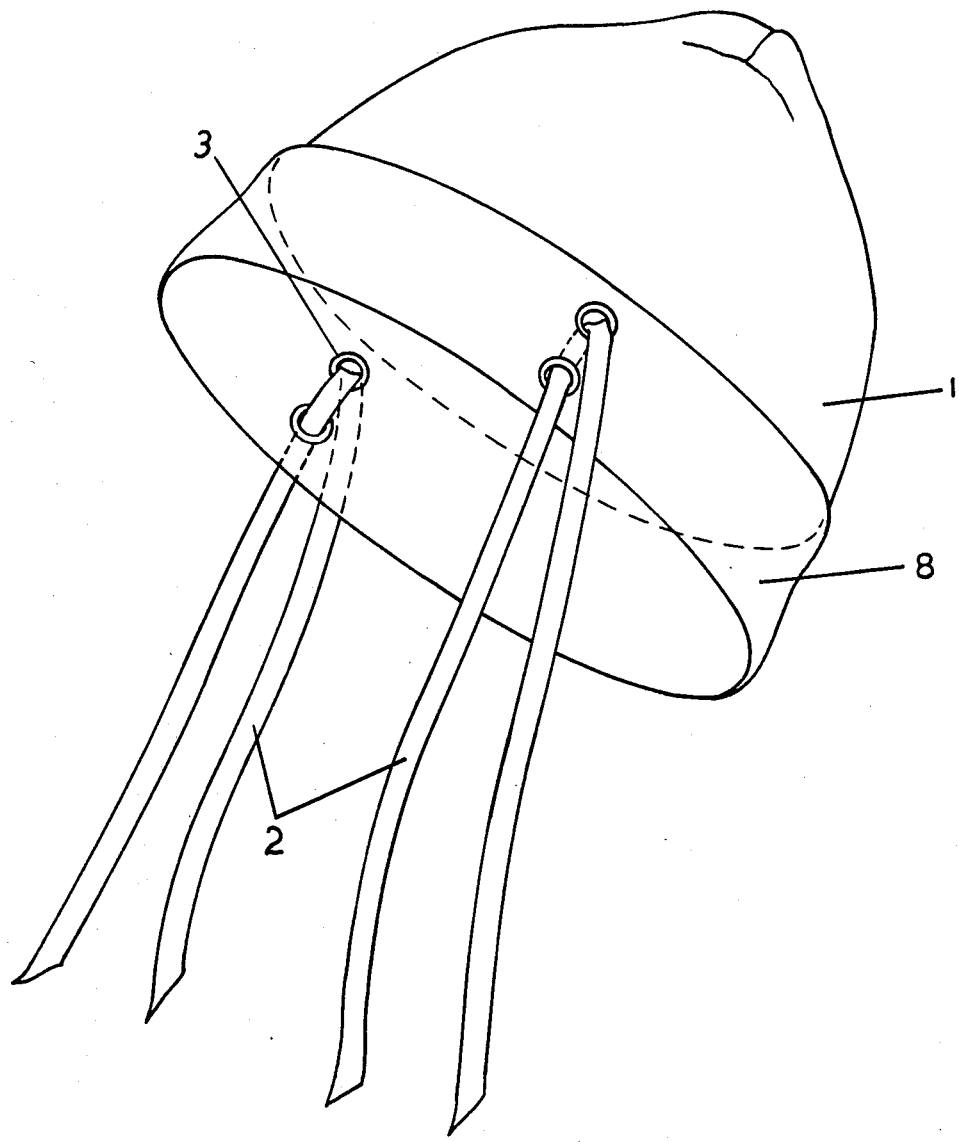
FIG. 1 is a perspective view of the device of the present invention.

Referring now to the drawings, there is shown in FIG. 1 a head covering 1, made of a material which generally conforms to the shape of a head. A preferred embodiment of the head covering is made of stockinette material, such as Burlington Stockinette, manufactured by Balfour, Inc., P.O. Box 610, Ashboro, N.C. 27203. However, any suitable material which adjusts to the shape of the head or provides the appropriate degree of stretch may be substituted for the stockinette material. It is desirable that the material be such that it is soft and comfortable to the patient's head and could be made of material which will aid in keeping the patient's head warm. The stockinette material is available in tubular form of varying diameters and lengths. Thus, the device of the present invention can be made to fit any individual head by choosing the appropriate diameter and length of stockinette.

Head covering 1 is made by enclosing one end of the tubular stockinette material by stitching or tying the edges together. However, any suitable method of enclosing the tubular material may be used. The opposite end of the tubular stockinette material is folded to the outside, forming reinforcement band 8 which encircles approximately the lower half of the circumference of head covering 1.

Head covering 1 is provided with two elongated thread-like members, such as straps 2 positioned approximately on opposite sides of head covering 1. Straps 2 may be permanently attached to head covering 1 by sewing the straps to the head covering or any other suitable means. However, a preferred method of attaching straps 2 to head covering 1 is by threading straps 2 through eyelets 3, eyelets 3 being permanently secured to head covering 1. The attachment points for straps 2 are located on the reinforced band 8 of head covering 1 at points which approximately correspond to the temporal areas of the patient's head. The proper points of attachment insure that the stress exerted by straps 2 is evenly distributed over the entire surface of the patient's head. As described above, this is an important feature of the device of the present invention since uneven application of pressure or stress can leave sores in the heads of small infants or cause molding of the infant's head.

Figure 2:
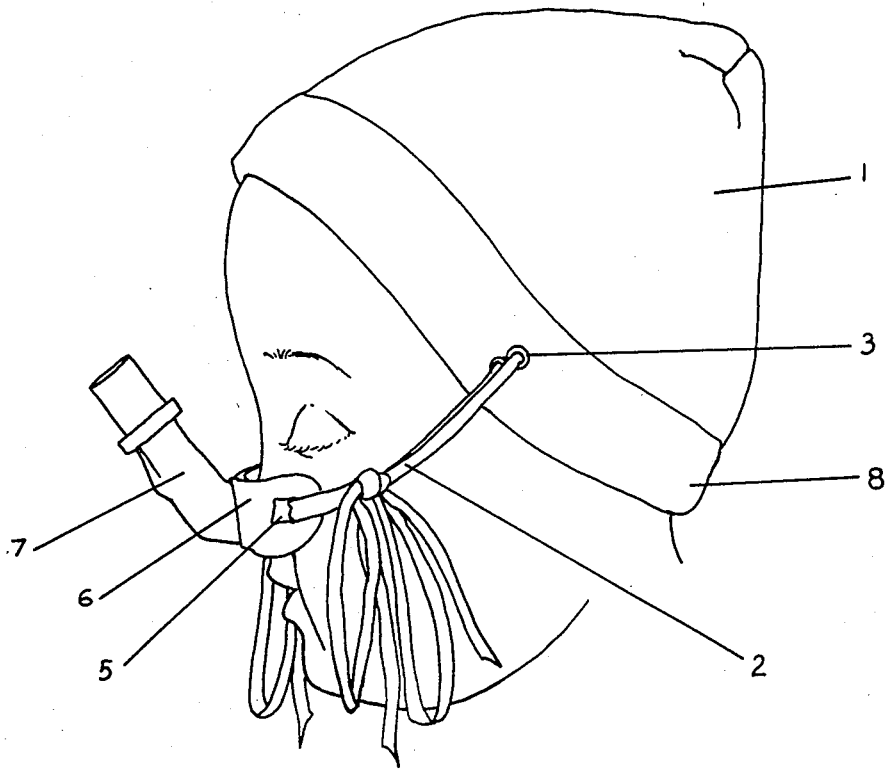
FIG. 2 is a side view of the device of the present invention in combination with a respiratory appliance.
Figure 3:
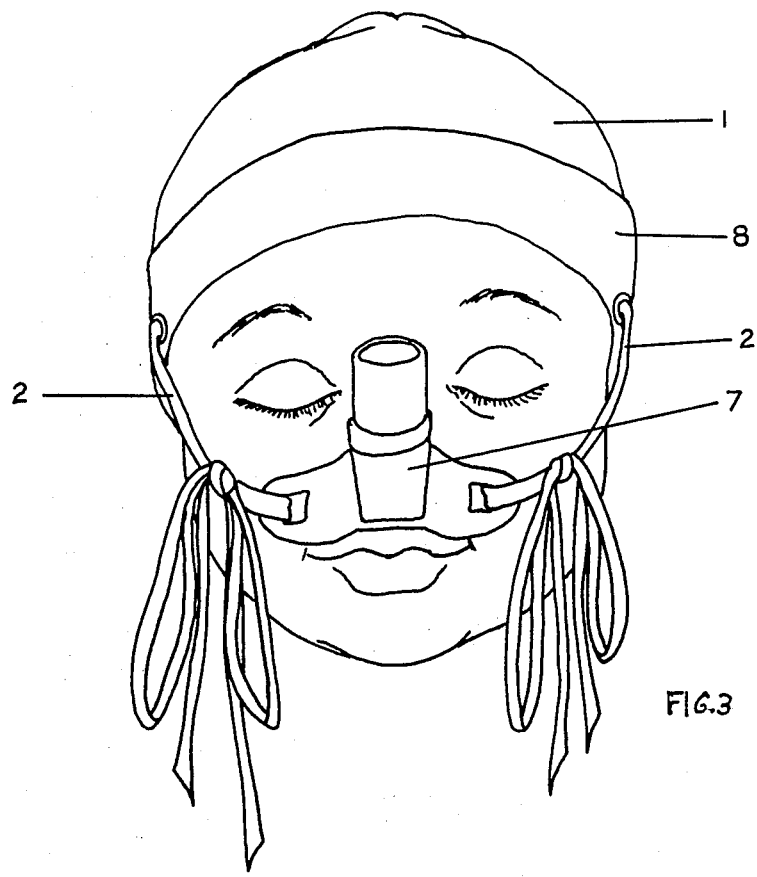
FIG. 3 is a frontal view of the device of the present invention in combination with a respiratory appliance.

As seen in FIGS. 2 and 3, straps 2 are threaded through opening 5 in extensions 6, which extend from either side of nasal prongs 7. Straps 2 then are securely tied in a bow or other suitable knot to secure nasal prongs 7 to the infant's airways. Although twill tape is suitable for use as straps 2 on the device of the present invention, any suitable material may be used for the straps 2. Further, other fasteners, such as VELCRO, may be used to secure straps 2 instead of the knot or bow.

The device of the present invention provides a means to attach a respiratory appliance to an infant in such a manner that the tugging pressure or stress resulting from attachment is evenly distributed over the head, decreasing the possibility of pressure sores, excoriation or molding. Further, the device of the present invention may be used to attach any medical device within an opening in the head of a patient to prevent slipping of the appliance during therapy. Thus, the correct position of the respiratory appliance is maintained within the opening, allowing maximum benefit of the appliance and minimizing the deleterious effects of malpositioning.

Although the device of the present invention is described a useful in aiding the application of continuous positive airway pressure to newborn infants, the device of the present invention can be manufactured in any size necessary to accommodate the needs of a patient. Further, the device of the present invention may be suitable for use in securing other respiratory appliances or therapeutic devices, such as, nasotracheal tubes and endo-tracheal tubes.

As will be readily understood by those of ordinary skill in the art, minor modifications may be made in the invention described above without in anyway departing from the spirit and scope of the invention. Accordingly, it is understood that the invention will not be limited to the exact details disclosed hereinabove, but will be defined in accordance with the appended claims.

What is claimed is:

1. A device for securing a nasally inserted respiratory appliance within the nares of a patient during respiratory therapy, the respiratory appliance defining securement openings, said device comprising
    a head covering formed substantially of resilient material and adapted to expand and contract to conform to different sized and shaped heads of various patients, retain that shape for the duration of the therapy and cover the entire head of the patient from the forehead to the base of the neck; and
    means for connecting said head covering to the respiratory appliance, said connecting means comprising at least two elongated members adapted for connecting the respiratory appliance to said head covering, one of the free-ends of each of said elongated members being adapted for insertion through one of the openings of the respiratory appliance, respectively, and adapted to be connected to its other free-end, said elongated members being attached to said head covering at opposite points thereon, respectively, which are adapted to approximately correspond to the temporal areas of the patient's head,
    said elongated members having means for adjusting the distance between the respiratory appliance and said head covering means so that the respiratory appliance is securely positioned within the nares of the patient, whereby when said head covering and said elongated members are positioned on the head of the patient and secured to the respiratory appliance the stress from the secured respiratory appliance is evenly distributed over the entire area of the patient's head.

2. A device according to claim 1 which further comprises a reinforcement band which overlies and parallels the peripheral edge of said head covering means.

3. A device according to claim 2 which further comprises eyelets for attaching said elongated members to said reinforcement band and said head covering, said eyelets being positioned at the opposite points on said head covering and extending through said reinforcement band and said head covering, and said eyelets receiving a free end of said elongated members, respectively.

4. A device according to claim 1 wherein said elongated members are two elongated thread-like members.

5. A device according to claim 1 wherein the respiratory appliance adapted to be secured by said device is nasal prongs which are used to administer respiratory therapy.

6. A system for administering respiratory therapy to a patient, said system comprises
    a head covering formed substantially of resilient material and adapted to expand and contract to conform to different sized and shaped heads of various patients, retain that shape for the duration of the therapy and cover the entire head of the patient from the forehead to the base of the neck;
    nasal prongs defining securement openings, said nasal prongs adapted to be positioned within the patient's nares and having means for connection to a source of respiratory gas; and
    at least two elongated members connecting said nasal prongs to said head covering, one of the free ends of each of said elongated members being inserted through one of the openings of the respiratory appliance, respectively, and connected to its other free end to vary the distance between said nasal prongs and said elongated head covering so that said nasal prongs are securely positioned within the nares, said elongated members being attached to said head covering at opposite points thereon, respectively, which are adapted to approximately correspond to the temporal areas of the patient's head.

* * * * *